United States Patent
Vogel et al.

(10) Patent No.: US 11,850,217 B2
(45) Date of Patent: Dec. 26, 2023

(54) ATHLETIC PERFORMANCE ENHANCEMENT COMPOSITION USING MENTHOL

(71) Applicant: Advanced Food Concepts, Inc., Berkeley, CA (US)

(72) Inventors: Roxanne Vogel, Berkeley, CA (US); Brandon Kirchmeyer, Berkeley, CA (US); Magdalena Boulet, Berkeley, CA (US)

(73) Assignee: Advanced Food Concepts, Inc., Berkeley, CA (US)

(*) Notice: Subject to any disclaimer, the term of this patent is extended or adjusted under 35 U.S.C. 154(b) by 232 days.

(21) Appl. No.: 17/320,504

(22) Filed: May 14, 2021

(65) Prior Publication Data

US 2021/0361589 A1    Nov. 25, 2021

Related U.S. Application Data

(60) Provisional application No. 63/027,486, filed on May 20, 2020.

(51) Int. Cl.

| | | |
|---|---|---|
| A61K 31/045 | (2006.01) | |
| A61K 31/198 | (2006.01) | |
| A61K 31/145 | (2006.01) | |
| A61P 43/00 | (2006.01) | |
| A61K 31/23 | (2006.01) | |
| A61K 9/00 | (2006.01) | |
| A61K 9/06 | (2006.01) | |

(52) U.S. Cl.
CPC .......... *A61K 31/045* (2013.01); *A61K 9/0056* (2013.01); *A61K 9/06* (2013.01); *A61K 31/145* (2013.01); *A61K 31/198* (2013.01); *A61K 31/23* (2013.01); *A61P 43/00* (2018.01)

(58) Field of Classification Search
CPC .................................................. A61K 31/045
See application file for complete search history.

(56) References Cited

U.S. PATENT DOCUMENTS

| | | | |
|---|---|---|---|
| 5,026,721 A * | 6/1991 | Dudrick | A61K 31/195 |
| | | | 514/561 |
| 5,908,864 A | 6/1999 | Casey | |
| 6,458,395 B1 | 10/2002 | Emoto | |
| 7,008,654 B1 | 3/2006 | Fuchs et al. | |
| 7,531,192 B2 | 5/2009 | Farber et al. | |
| 7,579,037 B2 | 8/2009 | Pons Biescas et al. | |
| 8,017,168 B2 | 9/2011 | Prakash et al. | |
| 8,496,958 B2 | 7/2013 | Harris et al. | |
| 8,937,049 B2 | 1/2015 | Stellingwerff et al. | |
| 9,730,462 B2 | 8/2017 | Gilkey et al. | |
| 9,872,871 B2 | 1/2018 | Jeppesen et al. | |
| 2003/0008046 A1 | 1/2003 | Gerlat et al. | |
| 2005/0095271 A1 | 5/2005 | Mathewson | |
| 2006/0280777 A1 | 12/2006 | Schydlowsky | |
| 2007/0190223 A1 | 8/2007 | Bordi, Jr. et al. | |
| 2013/0171294 A1 | 7/2013 | Martyn | |
| 2014/0234488 A1 | 8/2014 | Chang | |
| 2015/0038459 A1 | 2/2015 | Bacarella et al. | |
| 2016/0066610 A1 | 3/2016 | Garvey et al. | |

FOREIGN PATENT DOCUMENTS

| | | |
|---|---|---|
| CN | 1511479 A | 7/2004 |
| CN | 101731419 A | 6/2010 |
| EP | 1541042 B1 | 5/2006 |
| EP | 1853120 B1 | 9/2010 |
| EP | 1689256 B1 | 7/2011 |
| EP | 2098125 B1 | 10/2011 |
| WO | 99/62357 A1 | 12/1999 |
| WO | 2013/056048 A2 | 4/2013 |
| WO | 2016/112170 A1 | 7/2016 |
| WO | 2018/027070 A1 | 2/2018 |
| WO | 2018/027083 A1 | 2/2018 |
| WO | 2018/237000 A1 | 12/2018 |
| WO | 2019/094745 A1 | 5/2019 |
| WO | 2020/012480 A1 | 1/2020 |

OTHER PUBLICATIONS

Stevens et al. Sports Med., 2017, 47(6): 1035-1042.*
International Search Report dated Jul. 26, 2021 (12 pages).
Stevens, et al., Running performance and thermal sensation in the heat are improved with menthol mouth rinse but not ice slurry ingestion, Scand J Med Sci Sports Oct. 2016;26(10):1209-16.
Flood, et al., Oral L-menthol reduces thermal sensation, increases work-rate and extends time to exhaustion, in the heat at a fixed rating of perceived exertion, Eur J Appl Physiol. Jul. 2017;117(7):1501-1512.
Jeffries, Owen, Matthew Goldsmith, and Mark Waldron. "L-Menthol mouth rinse or ice slurry ingestion during the latter stages of exercise in the heat provide a novel stimulus to enhance performance despite elevation in mean body temperature." European journal of applied physiology 118.11 (2018): 2435-2442.
Barwood, M. J., et al. "Menthol as an Ergogenic aid for the Tokyo 2021 Olympic games: an Expert-Led consensus statement using the modified Delphi method." Sports Medicine 50.10 (2020): 1709-1727.

(Continued)

*Primary Examiner* — Rei Tsang Shiao
(74) *Attorney, Agent, or Firm* — Seyfarth Shaw, LLP

(57) ABSTRACT

The present invention is directed to an ingestible athletic performance enhancement composition comprising l-menthol wherein the composition does not contain alcohol. The present invention further includes athletic performance enhancement compositions wherein the amount of l-menthol is between 0.01 to 0.5 weight percent of the composition. The invention also includes methods of improving athletic performance comprising the ingestion of a composition comprising l-menthol, wherein the amount of l-menthol is sufficient to induce a cooling sensation while maintaining palatability and minimizing side effects.

20 Claims, No Drawings

(56) References Cited

OTHER PUBLICATIONS

Gavel, Erica H., et al. "Menthol Mouth Rinsing Is More Than Just a Mouth Wash—Swilling of Menthol to Improve Physiological Performance." Frontiers in Nutrition (2021): 404.

Keringer, Patrik, et al. "Menthol can be safely applied to improve thermal perception during physical exercise: A meta-analysis of randomized controlled trials." Scientific reports 10.1 (2020): 1-12.

Parton, Abbie Jayne, et al. "Thermo-behavioural responses to orally applied l-menthol exhibit sex-specific differences during exercise in a hot environment." Physiology & Behavior 229 (2021): 113250.

\* cited by examiner

ATHLETIC PERFORMANCE ENHANCEMENT COMPOSITION USING MENTHOL

BACKGROUND

It is well established that heat, and the perception of heat, negatively effects athletic performance. Hyperthermia, dehydration, cardiovascular strain, raised skin temperature, and decreased muscular activation are common responses to exercise in hot conditions. A variety of strategies have been studied to help mitigate these effects, including pre-cooling and cooling protocols. Water immersion and cold air exposure prior to exercise has been found effective in improving performance, as has the ingestion of an ice slurry as compared to cold water, prior to exercise and/or mid-exercise as a cooling means.

In addition to cooling techniques that lower body temperature, recent research has indicated that lowering the perception of thermal sensations of heat can increase endurance and performance even when body temperature and skin temperature are not in fact reduced. Improving the perception of thermal comfort and thermal sensation thus provides an additional avenue for improving athletic performance in hot conditions.

It has long been known that l-menthol, also known as natural menthol, 5-methyl-2-(propan-2-yl(cyclohean-1-ol), or simply menthol, results in a cooling sensation on the skin by stimulating cold receptors. This cooling sensation is psychologically on par to the action of spraying cold water on the face. Among other products, l-menthol is found in nasal inhalers, lotions, throat lozenges, shampoos, and is used to renew cooling "bandages" to lower skin temperature and decrease pain.

Application of l-menthol in topical form has been tested as a performance aid in sports and found beneficial. For example, applying a l-menthol body spray, for example, to a runner's clothing has been shown to lower the perception of exertion without otherwise effecting the core temperature of the athlete. As another example, scientists compared the performance effects of ingesting an ice-slurry before exercise with the performance effects using a l-menthol mouthwash designed to lower the thermal sensation of heat mid-exercise. The ice-slurry resulted in lower body temperature that was sustained for part of the exercise, but the effect on performance was not significant in comparison to those who were not treated. The use of the l-menthol mouthwash, on the other hand, resulted in significant improvement of running performance compared to the non-treated participants in the study. As a result of this study, the authors suggested addition of l-menthol to hydration and nutritional sports products. See Stevens, et al, *Running performane and thermal sensation in the heat are improved with menthol mouth rinse but not ice slurry ingestion,* 26(10) SCAND. J. MED. SCI. SPORTS 1209-1216 (October 2016).

While there has been a call for the development of l-menthol-enhanced food and beverage products for use in hydration and nutritional products for athletic performance enhancement, the use of l-menthol in ingestible products is not without challenges. While known as a flavoring, the compound, in improper dosages can cause drowsiness, vertigo, nausea and vomiting, and has the potential to trigger allergic reactions. L-menthol further contains a strong flavor profile that can overwhelm the overall taste of the product. L-menthol also presents as a crystal and can be difficult to dissolve, including but not limited to when the desired end product is a hydration and nutritional product for athletic performance enhancement. For example, while l-menthol dissolves in ethanol, the incorporation of alcohol is undesireable when the end use is for hydration and nutritional sports products.

There is a need for athletic performance enhancement products containing l-menthol that are effective in producing a cooling sensation while being palatable. There is also a need for such compositions to avoid containing alcohol. Further, there is a need for effective solvents to dissolve l-menthol crystals, including but not limited to solvents suitable for athletic performance enhancement products. Finally, there is a need for alcohol-free dissolution and processing of the l-menthol for compositions of athletic performance enhancement products.

SUMMARY

The present invention provides for ingestible compositions for athletic performance enhancement products, including but not limited to gels and liquids, that comprise l-menthol. The invention also provides for compositions for athletic performance enhancement products that avoid side effects associated with excessive menthol consumption.

Additionally, because it has been found that, once a threshold level of cooling sensation is reached, further menthol increases the intensity of the flavor and renders the product intolerable, the compositions of the present invention are directed to compositions comprising sufficient l-menthol to induce the cooling sensation while maintaining palatability.

The present invention further provides for compositions for athletic performance enhancement products that contain l-menthol in combination with other athletic performance enhancing components, including but not limited to amino acids. In certain non-limiting embodiments, the compositions of the present invention include l-menthol and branched-chain amino acids (BCAAs), i.e., l-isoleucine, l-leucine, and l-valine.

In one non-limiting embodiment of the present invention, l-menthol is present in an amount between about 0.01-0.5 weight percent of the composition for athletic performance enhancement products. In another non-limiting embodiment of the present invention, the composition for athletic performance enhancement products comprises l-menthol in an amount between about 0.01-0.5 weight percent of the composition in combination with one or more amino acids. In a further non-limiting embodiment of the present invention, the composition for athletic performance enhancement products comprises l-menthol in an amount between about 0.01-0.5 weight percent of the composition in combination with 1, 2, and/or all of the naturally occurring BCAAs. In another example, a composition for athletic performance enhancement product of the current invention comprises l-menthol in an amount between about 0.01-0.5 weight present of the composition in combination with about 2.5-10 weight percent of amino acids.

The present invention further includes, but is not limited to, compositions for athletic performance enhancement products that comprise menthol, but do not have alcohol. In another embodiment, the menthol crystals of the composition are dissolved using medium-chain trigyceride ("MCT") oil containing triglyceride fats. In additional embodiments, other non-water solvents are used to dissolve menthol in the development of the athletic performance enhancement product.

The present invention further includes methods of enhancing sports performance using ingestible compositions containing l-menthol wherein the amount of l-menthol is sufficient to induce the desired cooling sensation while maintaining palatability.

DETAILED DESCRIPTION OF THE INVENTION

The present invention relates to compositions for athletic performance enhancement products that may be consumed in liquid, slurry, gel, semi-solid, and solid forms to improve sports performance, particularly in hot conditions. The compositions of the present invention comprise l-menthol, preferably natural l-menthol.

In non-limiting embodiments of the present invention, l-menthol is present in the composition for an athletic performance enhancement product in an amount between about 0.01-0.5 weight percent of the composition, about 0.01-0.1 weight percent of the composition, about 0.03125-0.125 weight percent, about 0.1-0.25 weight percent, about 0.25-0.4 weight percent, about 0.4-0.5 weight percent of the compound, about 0.03125 weight percent of the composition, about 0.05 weight percent of the composition, about 0.0625 weight percent of the compound, about 0.1 weight percent of the composition, about 0.125 weight percent of the composition about 0.2 weight percent of the composition, about 0.25 weight percent of the composition, about 0.3 weight percent of the composition, about 0.4 weight percent of the composition, about 0.45 weight percent of the composition, or about 0.5 0 weight percent of the composition. As one non-limiting example, the amount of l-menthol in the composition of the current invention is 0.46 weight percent of the composition. In one embodiment, the amount of l-menthol in a 32 g serving size is present in the composition for an athletic performance enhancement product in an amount between about 3.2-160 mg, about 3.2-10 mg, about 10-40 mg, about 40-100 mg, about 100-150 mg., about 150-160 mg, about 10 mg, about 20 mg, about 30 mg, about 40 mg, about 100 mg, about 150 mg, or about 160 mg. In one non-limiting example, the amount of l-menthol in the composition of the current invention is 20 mg in a 32 g serving size.

The l-menthol in the composition may come from any source, including but not limited to natural or synthetic l-menthol. As non-limiting examples, only, l-menthol may be obtained and/or synthesized from the oils of mints, including but not limited to peppermint, spearmint, corn mint, apple mint, water mint, wild mint, and/or pennyroyal, by means known in the art.

L-menthol is a crystalline compound. In some compositions of the present invention, the l-menthol is dissolved in non-water solvents. As one non-limiting example, l-menthol is combined with MCT oil for dissolution purposes. In another example, l-menthol is combined with glycerol for dissolution purposes.

Certain embodiments of the present invention are directed to compositions for athletic performance enhancement products that comprise l-menthol in combination with one or more amino acids. As examples, the compositions of the present invention may include, but are not limited to, compositions comprising l-menthol and branched-chain amino acids (BCAAs), i.e., l-isoleucine, l-leucine, and l-valine. Some embodiments of the present invention comprises l-menthol and one or more amino acids, where the amount of the one or more amino acids combined is about 2.5-10 weight percent of the composition, about 2.5-5 weight percent of the composition, about 5-7.5 weight percent of the composition, about 7.5-10 weight percent of the composition, about 2.5 weight percent of the composition. about 3.5 weight percent of the composition, about 4.5 weight percent of the composition, about 5.5 weight percent of the composition, about 6.5 weight percent of the composition, about 7.5 weight percent of the composition, about 8.5 weight percent of the composition, about 9.5 weight percent of the composition, or about 10 weight percent of the composition. In one embodiment, the combined amount of one or more amino acids of the composition is about 4.6% weight percent of the composition. In one embodiment, the combined amount of amino acids in a 32 g serving size is present in the composition for an athletic performance enhancement in an amount between about 0.8-3 g, about 0.8-1.5 g, about 1.2-2.7 g, about 2.5-3 g, about 1.5 g., about 2.0 g, or about 2.5 g. In one non-limiting example, the combined amount of amino acids in the composition of the current invention is 1.425 g in a 32 g serving size. In another non-limiting example, the amount of l-menthol in the composition of the current invention is 20 mg in a 32 g serving size and the combined amount of amino acids in said composition is 1.425 g.

In another embodiment, the invention may include, but is not limited to, compositions comprising l-menthol in an amount 0.01-0.25 weight percent of the composition and amino acids in a combined amount of 0.025-0.1 weight percent of the composition. In one non-limiting embodiment, the composition comprises l-menthol in an amount of 0.0625 weight percent of the composition and amino acids in a combined amount of 4.6% weight percent. In another non-limiting example, the amount of l-menthol in the composition of the current invention is 20 mg in a 32 g serving size and the combined amount of amino acids in said composition is 1.425 g. In certain non-limiting embodiments, the compositions of the present invention the amino acids combined with l-menthol are branched-chain amino acids (BCAAs), selected from one or more of l-isoleucine, l-leucine, and l-valine.

The present invention also provides for compositions for athletic performance enhancement products that avoid side effects associated with excessive menthol consumption. It has been found that, once a threshold level of cooling sensation is reached, further menthol increases the intensity of the flavor and renders the product intolerable, the compositions of the present invention are directed to compositions comprising sufficient menthol to induce the cooling sensation while maintaining palatability. To obtain cooling effects without the presence of side effects or compromising taste, the amounts of l-menthol in such compositions of the present invention are between 0.01% to 0.5% weight percent of the composition.

The present invention further includes compositions for athletic performance enhancement products that comprise menthol, but do not have alcohol.

Additional compositions of the present invention comprise l-menthol dissolved in non-water solvents. In one non-limiting example, l-menthol is combined with MCT oil. In another non-limiting embodiment, l-menthol is combined with glycerol. In certain embodiments, additional embodiments, other non-water solvents are used to dissolve menthol prior to the development of the nutritional sports product. In certain embodiments, additional embodiments, other non-water solvents are used to dissolve menthol prior to the development of the athletic performance enhancement product.

Other components that may be added to the composition of the present invention in addition to l-menthol and may include, but are not limited to, electrolytes, such as sodium, potassium, magnesium, calcium, bicarbonate, chloride, phosphate or the like; minerals and elements; vitamins; sugar and/or sugar substitutes; natural flavors; and/or preservatives. Such components other than l-menthol mentioned herein may be present in any form suitable for ingestion. By way of example only, forms of electrolytes may include, but are not limited to, sodium citrate, sea salt, potassium citrate, and/or calcium carbonate.

Table 1 describe components of a suitable composition of an athletic performance enhancement product:

TABLE 1

32 g serving size: Nutritional information on gel comprising, among other components, l-menthol and further comprising amino acids.

| Ingredient | Amount per serving |
|---|---|
| Calories | 100 calories |
| Total Carbohydrates | 21 g |
| Calcium | 30 mg |
| Sodium | 125 mg |
| Amino Acid blend - L-leucine, taurine, l-valine, beta-alanine, l-isoleucine | 1425 mg |
| l-menthol | 20 mg |

In an embodiment of the present invention, the caloric intake of the supplement is less than about 150 calories, less than 100 calories, less than about 50 calories, about 100 calories, or about 150 calories per serving.

Example 1

A composition of the formula depicted in Table 1 was prepared.

Testing

The present invention further includes methods of enhancing sports performance using compositions containing l-menthol wherein the amount of l-menthol is sufficient to induce the desired cooling sensation while maintaining palatability and minimizing side effects.

Pilot studies using example compositions have been conducted to evaluate the effects of the amount of l-menthol on the cooling sensation and palatability of the product.

Pilot Study 1

In pilot study 1, 10 elite and pre-elite race walkers, including Olympians and Australian gold and silver medalists, tested three gels: (A) a gel containing l-menthol at a concentration of 0.5 weight percent, (B) a gel containing l-menthol at a concentration of 0.1%, and (C) a placebo gel lacking l-menthol. A double-blind protocol was adopted. Athletes ingested the gels separately in randomized order during three different 'long walk' training sessions of 15-25 km where the temperature was between 23-26 degrees Celsius and 65%-75% relative humidity. In each training session, athletes were provided with two of the same gel type and consumed such gels with water after completing 50-80% of the goal distance during the training session.

After each training session, the athletes were surveyed on flavor, intensity, cooling sensation, sweetness, and overall experience. With respect to flavor, the athletes were asked how much the product tasted like a mint confection, with the values of 1=not at all, 2=slightly, and 3=very much. Gel B was rated as the sample that tasted most like a mint confection (2.8/3).

With respect to intensity, the athletes were asked to rate the intensity of the mint flavor, with the values of 1=too weak, 2=slightly weak, 3=about right, 4=a little strong, and 5=too strong. Gel A was rated as the most intense and on average "a little strong" (4.1/5). Gel B was rated on average as "about right" (3.2/5).

With respect to cooling sensation, the athletes were asked to rate the intensity of the cooling sensation with the value of 1=very mild/absent, 2=mild, 3=moderate, 4=slightly intense, and 5=too intense. Gel A was rate as slightly intense (4.1/5) and Gel B was rated as between moderate and slightly intense (3.7/5). The placebo was, as expected, rated as less than mild.

With respect to sweetness, the athletes were asked to rate the overall sweetness with the values of 1=not sweet enough, 2=almost sweet enough, 3=about right, 4=a little too sweet, and 5=much too sweet. Both Gel A and Gel B were rated as "about right" for sweetness (3.2/5). Gel C was rated closer to "a little too sweet" (3.6/5).

With respect to the overall experience, the athletes were asked about their overall experience using the sample gel with the values of 1=dislike, 2=slightly dislike, 3=indifferent, 4=like, 5=like very much. Gel B was rated highest with a value close to "like" (3.7/5). The athletes were on average indifferent about Gel A (2.9/5).

One athlete experienced gastrointestinal distress as a result of Gel A and Gel B, with the effects of Gel B lasting for only a few minutes compared to Gel A.

Pilot Study 2

In pilot study 2, 30 elite and pre-elite athletes consisting of 15 race walkers, 19 cyclists, and 6 runners, tested the same three gel compositions as in Pilot Study 1, i.e., three gels: (A) a gel containing l-menthol at a concentration of 0.5 weight percent, (B) a gel containing l-menthol at a concentration of 0.1%, and (C) a placebo gel lacking l-menthol. A double-blind protocol was adopted.

Athletes ingested the gels separately in randomized order. The race walkers and runners tested the gels during training sessions and the cyclists tested the gels during local club races or training. Gels were consumed before, during, and/or after exercise during summer.

After each training session/race, the athletes were surveyed on flavor, intensity, cooling sensation, sweetness, and overall experience using the same scales and criteria as in Pilot Study 1. With respect to flavor, the athletes were asked how much the product tasted like a mint confection, with the values of 1=not at all, 2=slightly, and 3=very much. Gel B was rated as the sample that tasted most like a mint confection (2.6/3).

With respect to intensity, the athletes were asked to rate the intensity of the mint flavor, with the values of 1=too weak, 2=slightly weak, 3=about right, 4=a little strong, and 5=too strong. Gel A was rated as the most intense and on average "a little strong" (4.4/5). Gel B was rated on average as between "about right" and "a little strong" (3.6/5).

With respect to cooling sensation, the athletes were asked to rate the intensity of the cooling sensation with the value of 1=very mild/absent, 2=mild, 3=moderate, 4=slightly intense, and 5=too intense. Gel A was rate as slightly intense (4.3/5) and Gel B was rated as between moderate and slightly intense (3.5/5). The placebo was, as expected, rated as less than mild.

With respect to sweetness, the athletes were asked to rate the overall sweetness with the values of 1=not sweet enough, 2=almost sweet enough, 3=about right, 4=a little too sweet, and 5=much too sweet. All three gels were rated on average as "about right" for sweetness, but the presence of l-menthol slightly lowered the perception of sweetness With respect to the overall experience, the athletes were asked about their overall experience using the sample gel with the values of 1=dislike, 2=slightly dislike, 3=indifferent, 4=like, 5=like very much. Gels B and C were rated on average between "indifferent" and "like" (3.2/5 for Gel B; 3.5/5 for Gel C). Gel A was rated closer to "dislike" (2.2/5).

Three athletes experienced gastrointestinal distress as a result of Gel A. For two of those athletes, Gel B was found to cause gastrointestinal distress that lasted less time than Gel A.

Although the present inventions and their advantages have been described in detail, it should be understood that various changes, substitutions and alterations can be made herein without departing from the spirit and scope of the disclosure as defined by the appended claims. Moreover, the scope of the present application is not intended to be limited to the particular compositions of matter, means, methods and steps described in the specification. As one of ordinary skill in the art will readily appreciate from the present disclosure, the compositions of matter, means, methods, or steps, presently existing or later to be developed that perform substantially the same function or achieve substantially the same result as the corresponding examples described herein may be utilized according to the present disclosure. Accordingly, the appended claims are intended to include within their scope such compositions of matter, means, methods, or steps.

The invention claimed is:

1. An athletic performance enhancement composition for ingestion comprising l-menthol in an amount of about 0.01 to 0.5 weight percent of the composition, wherein said composition does not include ethanol.

2. The athletic performance enhancement composition of claim 1, wherein the composition is in the form of a gel, slurry, or liquid.

3. The athletic performance enhancement composition of claim 2, wherein the composition is in the form of a gel.

4. The athletic performance enhancement composition of claim 1, wherein the composition is in the form of a semi-solid or solid.

5. The athletic performance enhancement composition of claim 1, wherein the composition further comprises MCT oil.

6. The athletic performance enhancement composition of claim 3, wherein the composition further comprises MCT oil.

7. The athletic performance enhancement composition of claim 1, wherein the composition further comprises at least one amino acid.

8. The athletic performance enhancement composition of claim 2, wherein the composition further comprises at least one amino acid.

9. The athletic performance enhancement composition of claim 6, wherein the composition further comprises at least one amino acid.

10. The athletic performance enhancement composition of claim 7, wherein the total combined amount of amino acids is 2.5 to 10 weight percent of the composition.

11. The athletic performance enhancement composition of claim 8, wherein the total combined amount of amino acids is 2.5 to 10 weight percent of the composition.

12. The athletic performance enhancement composition of claim 9, wherein the total combined amount of amino acids is 2.5 to 10 weight percent of the composition.

13. The athletic performance enhancement composition of claim 7, wherein the amino acids comprise one or more branched chain amino acids.

14. The athletic performance enhancement composition of claim 10, wherein the amino acids comprise one or more branched chain amino acids.

15. The athletic performance enhancement composition of claim 11, wherein the amino acids comprise one or more branched chain amino acids.

16. An athletic performance enhancement composition for ingestion comprising l-menthol in an amount of about 0.01 to 0.5 weight percent of the composition and one or more amino acids in the combined amount of 2.5 to 10 weight percent of the composition, wherein said composition does not include ethanol, and wherein said composition is in the form of a gel, slurry, or liquid.

17. The athletic performance enhancement composition of claim 16, wherein the composition further comprises MCT oil.

18. The athletic performance enhancement composition of claim 16, wherein the amount of l-menthol is about 0.0625 weight percent of the composition and the combined amount of the one or more amino acids is 4.6 weight percent of the composition.

19. A method of improving athletic performance comprising the ingestion of a composition comprising l-menthol, wherein the amount of l-menthol is sufficient to induce a cooling sensation while maintaining palatability and minimizing side effects, and further wherein the composition does not contain ethanol.

20. The method of improving athletic performance of claim 19 wherein the amount of l-menthol is about 0.01 to 0.5 weight percent of the composition.

* * * * *